United States Patent
Geistlich et al.

(10) Patent No.: US 6,676,969 B2
(45) Date of Patent: Jan. 13, 2004

(54) RESORBABLE EXTRACELLULAR MATRIX FOR RECONSTRUCTION OF CARTILAGE TISSUE

(75) Inventors: Peter Geistlich, Stansstad (CH); Myron Spector, Boston, MA (US); Zdenek Eckmayer, Weinheim (DE)

(73) Assignee: Ed. Geistlich Soehne AG fuer Chemische Industrie (CH)

( * ) Notice: Subject to any disclaimer, the term of this patent is extended or adjusted under 35 U.S.C. 154(b) by 0 days.

(21) Appl. No.: 09/986,757

(22) Filed: Nov. 9, 2001

(65) Prior Publication Data

US 2002/0048595 A1 Apr. 25, 2002

Related U.S. Application Data

(63) Continuation-in-part of application No. 08/894,517, filed as application No. PCT/GB96/00399 on Feb. 22, 1996, now Pat. No. 6,326,029.

(30) Foreign Application Priority Data

Feb. 22, 1995 (GB) ............................................. 9503492

(51) Int. Cl.⁷ ........................... A61K 9/10; A61K 47/42
(52) U.S. Cl. ...................................... 424/484; 424/428
(58) Field of Search ................................ 424/484, 548, 424/356, 428; 530/412, 422, 425, 426, 427

(56) References Cited

U.S. PATENT DOCUMENTS

| | | | |
|---|---|---|---|
| 5,162,430 A | 11/1992 | Rhee et al. | |
| 5,206,023 A | 4/1993 | Hunziker | |
| 5,523,348 A | 6/1996 | Rhee et al. | |
| 5,541,295 A | * | 7/1996 | Barrach et al. |

FOREIGN PATENT DOCUMENTS

| AU | B660045 | 6/1995 |
|---|---|---|
| AU | B663150 | 9/1995 |
| FR | 2679778 | 2/1993 |
| WO | 9005755 | 5/1990 |
| WO | 9013302 | 11/1990 |
| WO | 9213565 | 8/1992 |
| WO | 9310722 | 6/1993 |
| WO | 9311723 | 6/1993 |
| WO | 9319168 | 9/1993 |
| WO | 9518638 | 7/1995 |

\* cited by examiner

*Primary Examiner*—Edward J. Webman
(74) *Attorney, Agent, or Firm*—Rothwell, Figg, Ernst & Manbeck PC

(57) ABSTRACT

A resorbable extracelluar matrix for reconstruction of cartilage tissue includes a purified collagen II derived from natural cartilage tissue from which non-collagen proteins have been removed.

3 Claims, No Drawings

RESORBABLE EXTRACELLULAR MATRIX FOR RECONSTRUCTION OF CARTILAGE TISSUE

CROSS-REFERENCE TO RELATED APPLICATIONS

This is a continuation-in-part of U.S. Ser. No. 08/894,517, filed Nov. 10, 1997, now U.S. Pat. No. 6,326,029 which is a §371 of International Application No. PCT/GB96/00399, filed Feb. 22, 1996, claiming priority from United Kingdom Patent Application 9503492.2, filed Feb. 22, 1995.

DETAILED DESCRIPTION OF THE INVENTION

The present invention concerns an extracellular matrix for reconstruction of cartilage tissue.

In tissue engineering, it has long proved difficult to reconstruct cartilage. Reconstruction of tissue, in general, comprises provision of a matrix which serves as a guide for cells which grow along and between the fibres of the matrix. Hitherto, attempts to reconstruct cartilage, using matrices based on polylactic acid, polyglycolic acid and collagen I or III, required the matrices to be loaded in vitro with chondrocytes prior to implantation of the loaded matrix in an appropriate in vivo site. It had not proved possible simply to implant the matrices of this type at the in vivo site and rely on growth of the native chondrocites on the surface of the matrix. The need to load the matrix with chondrocytes in vitro prior to implantation gave rise to complications and difficulties in terms of the sterile culture of the chondrocytes.

There is thus a need for a matrix implant for reconstruction of cartilage tissue which will permit in-growth of native chondrocytes after implantation in vivo. We have now found that these requirements may be met by a matrix of collagen fibres, provided that the collagen is predominantly collagen II.

Collagen occurs in a number of forms in the animal body and different tissues contain different proportions of the respective types. Thus, whereas bone collagen comprises predominantly collagen I and III, cartilage comprises predominantly collagen II together with smaller quantities of collagen VI, IX, X, XI and XIII. Such material differs significantly from collage sponge material used in medicine and in cosmetics which, being derived from skin and tendons consists of collagen I and/or III.

According to one aspect of the present invention, therefore, there is provided a resorbable extracellular matrix for reconstruction of cartilage tissue comprising predominantly fibres of collagen II.

As indicated above, such a matrix may contain minor quantities of collagen VI, IX, X, XI and XIII. The matrix according to the invention desirably also contains a hydrogel-like material, for example comprising glycosaminoglycans such as chondroitin sulphate, keratan sulphate, dermatan sulphate and hyaluronic acid, which provides a natural medium in which chondrocytes can become embedded and grow in general, the matrix according to the invention preferably contains 0.1 to 40% by weight of glycosaminoglycan, for example 5–15% e.g. about 10% by weight.

The matrix according to the invention may either comprise natural cartilage material which has been subjected to defatting and other treatment, leaving the collagen II material together with glycosaminoglycans, or alternatively fibres of purified collagen II may be mixed with glycosaminoglycans and any other required additives. Such additional additives may, for example, include chondronectin or anchorin II to assist attachment of the chondrocytes to the collagen II fibres and growth factors such as cartilage inducing factor (CIF), insulin-like growth factor (IGF) and transforming growth factor β (TGFβ).

There exists a wide range of glycosaminoglycans and proteoglycans which have different and sometimes undesirable properties. Thus, although it is possible to incorporate into the collagen matrix glycosaminoglycans from different sources which do not have the same composition, molecular weight and physiological properties as glycosaminoglycans from cartilage, it is particularly preferred to use glycosaminoglycans from cartilage itself.

It is desirable to subject the collagen matrix to some degree of cross-linking in order to restrict the extent of swelling when the matrix comes in contact with aqueous fluids, while retaining the ability of the matrix to be resorbed. Such swelling leads to loss of strength and shape. However, chemical cross-linking at may present physiological disadvantages in terms of pore size which could negatively influence the properties of the collagen. The pore size should optionally be around $0.4\mu$ in order to promote chemotaxis and other functions of the cells. The collagen matrix according to the invention may advantageously be manufactured by subjecting cartilage tissue to defatting followed by treatment with a base whereby proteoglycans and glycosaminoglycans are removed.

The cartilage material will normally be that from readily available animal sources such as cattle, sheep or pigs. The preferred material is hyaline cartilage from pigs. This contains the right type of collagen and glycosaminoglycan in desirable proportions and is available in suitably large quantities.

The cartilage is preferably frozen after slaughter and subjected to size reduction, for example to a particle diameter of about 8 mm. Before size reduction, the cartilage is preferably soaked in water and mechanically separated from flesh, bone and other unwanted materials.

The particulate cartilage is then preferably subjected to dewatering by treatment with a water miscible organic solvent such as acetone, which also serves to remove some fat. The dewatering shrinks the collagen fibres and separates them from each other so that the subsequent defatting step is optimised. The material is then subjected to defatting with a fat-solvent such as a hydrocarbon e.g. hexane, or a halogenated hydrocarbon.

After defatting, the material is thoroughly washed and this is continued until as much water has been taken up as was present originally. By this procedure, the material is optimised for the base-treatment which follows.

The base-treatment may be effected with a strong alkali, for example and alkali metal hydroxide, eg. sodium hydroxide, for example at a concentration of 1–8% by weight. The treatment time, which will vary according to the raw material and alkali concentration, is generally 10–48 hours. The treatment temperature will generally be below 20° C. The pH value is normally in the range 12–14. The above conditions are those which are optimal for treatment with NaOH. Treatment with other bases may require slightly modified conditions.

The base-treatment has the following effects:

Small quantities of residual fat are saponified.

The non-collagen, alkali soluble proteins are denatured, destroyed, dissolved and eliminated.

The amide groups in the collagen are saponified, thereby changing the electric charge and the isoelectric point of the collagen.

Bacteria, prions and viruses are inactivated and the collagen is thus sterilised.

It has been found that by this treatment, proteoglycans undergo a useful modification which can be characterised as follows:

the covalent binding of glycosaminoglycans to the core protein in proteoglycans is cleaved. In this way the glycosaminoglycans can be liberated from the protein of the proteoglycans. This is termed β-elimination.

By the base-treatment, the core protein is split into small peptides which may be removed from the reaction mixture by dialysis or ultra filtration.

Due to the strong negative charge, the glycosaminoglycans form water soluble salts which can partially washed from the collagen. These are, however, uncleaved or only slightly cleaved by the base-treatment and can be separated from peptides by dialysis. A part of the glycosaminoglycan (about 3% by weight of the collagen) is bound to the collagen.

Purified glycosaminoglycans may be obtained by dialysis or ultrafiltration of the extract arising from the base-treatment step.

According to the procedure of the present invention, enzymatic treatment is, in general, not used, in view of the variety of different substances present. However, further steps include treating the material with an organic or inorganic acid, such as hydrochloric acid. This has the following effect:

Unwanted acid sensitive materials are removed;

The fibre structure is loosened.

Subsequently, the material is washed, generally until the pH value of the material is between 2.5 and 4.0. The pH value of the material is preferably controlled accurately. The pH value of the material should be uniform across the cross-section of the cartilage.

After the acid treatment, the cartilage is in a water-swelled condition. The material is then subjected to mechanical size-reduction, for example using a colloid mill. The concentration of the collagen in the aqueous medium is then about 2.5–3.5% by weight. The pH value of this mixture should be somewhat acid, for example 3.5–4.5.

At this point, glycosaminoglycan may be added to the purified collagen mass, for example in the range 0.1–40% preferably 5 to 15%, of the weight of collagen.

The glycosaminoglycan added to the collagen is preferably that extracted from the natural cartilage, as indicated above. The matrix will then contain, besides collagen II, the glycosaminoglycans hyaluronic acid, chondroitin sulphate and keratan sulphate. The chondroitin sulphate and keratan sulphate are covalently bonded to the core protein while hyaluronic acid is, indeed, bound to the proteoglycan but not covalently. By the action of the base, the bonding to the core protein is cleaved and the glycosaminoglycan is freed from the protein. Additionally, the core protein is cleaved to small peptides which are readily removed by dialysis or ultrafiltration. It is important that the core protein is removed, since this may be immunologically active. The removal of the core protein is thus an important part of the process of the present invention.

The recovery of the glycosaminoglycans from the base extract may be effected as follows:

The medium is neutralised to a pH value in the range 6–8.

The non-collagen proteins are removed by treatment with an adsorbent such as kaolin.

Ultrafiltration of the liquid is effected, using a membrane which permits the passage of molecules of weight les than 10000 daltons.

Concentration of the liquid is effected to a solids content of about 2–5 weight percent.

After admixture of the glycosaminoglycan with the collagen II, the material is homogenised still further in a colloid mill and the solid content is adjusted to 1.5–2.5 weight percent. This mass can then serve for the production of two types of product, namely a sponge or a collagen sheet.

For the production of a sponge, the mass resulting from homogenisation is frozen. The freezing must be precisely controlled, whereby the freezing time, pH value and particle size are exactly maintained in order to provide a reproducible pore size. The frozen product is then freeze-dried. After freeze-drying, the sponge is warmed to 120–140° C. for at least 2 hours. In this way, the material is stabilised by light cross-linking. After the freeze-drying the material is cut to a desired thickness, stamped to the required shape, sterilised and packed.

Because the use of sponges is limited for use in some fields due to insufficient strength, the collagen matrix according to the invention can advantageously be used for the production of collagen sheets, which are suitable for use in a wide range of medical indications.

For the production of collagen sheets, the concentration of purified II collagen fibres in the liquid suspension should be in the range 0.2–3 weight percent, advantageously 0.5–2 weight percent. Air is preferably removed.

A gel is then formed as an intermediate step. The production of the collagen gel can be effected by various techniques known for gel formation.

The gel is then dried, normally on a plate. In this way, not only is water removed but insoluble collagen-glucosaminoglycan products are formed which are very beneficial for the growth of cells.

For either the above products, the matrix according to the invention can be supplemented with active substances. Thus any physiologically active substance which is water soluble or water dispersible can be used. Thus, the matrix may advantageously contain medicinal substances such as antibacterials, eg. taurolidine, or antibiotics such as tetracyclines and gentamycins.

The invention also provides the use of a matrix according to the invention in guided regeneration of cartilage tissue.

The following examples are given by way of illustration only:

EXAMPLE 1

Frozen cartilage from freshly slaughtered pigs was steeped in cold water, thoroughly washed through and mechanically purified from flesh residues, bones and hard pieces. Subsequently, the material was washed for 30 minutes under flowing water.

Subsequently, the material was ground three times in a homogenizer. The optical particle size at the end of size reduction was about 8 mm.

The cartilage pieces were dewatered by washing 4 times with acetone, each time for 8 hours. The cartilage was then defatted by extraction 4 times with n-hexane. Each treatment lasted at least 8 hours. The ratio of hexane to cartilage was 1:10.

After defatting, the cartilage was swelled in drinking water. The ratio of water:material was 10:1. The treatment time was 24 hours.

The material was then treated with NaOH (5% by weight) whereby the ratio of cartilage to liquid was 1:4 and the treatment time was 32 hours. During the treatment, the pieces of cartilage were well stirred. Subsequently, the alkali was washed from the cartilage. The original pH of 14 was thereby reduced to 9–11. The dissolved impurities were washed out and separated from the cartilage. The liquid resulting from the alkaline treatment was collected for the recovery of glycosaminoglycan.

The collagen material was then treated with strong HCl (about 3% by weight) initially at a pH value under 1.0. The treatment time was 4–6 hours.

Subsequently, the material was washed with cold water long enough for the pH value to rise to 3–3.5. All impurities were removed and the product was a salt-free collagen mass, suitable for production of a sponge or other collagen material. For that purpose, the cartilage mass may be, according to the intended result, degassed, frozen and freeze-dried.

EXAMPLE 2

The extract resulting from alkaline treatment in Example 1 contained glycosaminoglycan, alkali, denatured proteins and salts. The extract was firstly neutralised with HCl, the pH value after neutralisation being 6. The extract was then treated with a filter aid, namely kieselguhr, which had the effect of removing the denatured proteins. 0.5 weight percent of kieselguhr was introduced into the extract and removed by filtration together with the denatured protein.

The supernatant was then submitted to ultrafiltration using a membrane having a molecular weight cut off at about 10000 daltons. In this way, salts were removed to leave purified glycosaminoglycan.

The glycosaminoglycan solution so obtained was admixed with collagen material from above to provide a collagen II matrix containing glycosaminoglycan.

EXAMPLE 3

(1) Determination of Hexosamine and Amino Acid Residues in Collagen Sponges and Fleeces Each sample, exactly weighed (about 10 mg) was hydrolised in 10 ml of 3M or 6M HCl at 1.05° C. for 15 or 20 hours under purified nitrogen in a sealed tube. After cooling the tube in a refrigerator and opening the tube, the contents were transferred to a 25 ml long neck flask and dried at 40° C. in a vacuum-rotation dryer (Rotavapor RE120, Büchi, Switzerland) under water jet vacuum. After dissolving the residue in 5 ml water, the residue was again dried under water jet vacuum. Subsequently, the residue was taken up in 5 ml loading buffer (0.2M relative to Na+) at pH 2.2. For determination of the glucosamine and galactosamine values, after previous dilution of an aliquot with loading buffer (1+10) 150 $\mu$l of the sample hydrolysed in 3M HCl was injected into the cartouche of an amino acid analyser (AlphaPlus, type 4151, Pharmacia-LKB, Freiburg) and evaluated by comparison with a standard with the help of a computer (Shimadzu, Dusseldorf). The same procedure was effected with the sample hydrolised in GM HCl, wherein 50 $\mu$l were injected in a further test cartouche. The double hydrolysis in 3M and GM HCl is necessary for optimisation of the hexosamine and amino acid analysis since the maximal values for hexosamine and also tyrosine are only obtained after hydrolysis in 3M HCl while maximal values are only obtained for valine, isoleucine and leucine after hydrolysis in 6M HCl.

2. Determination of Native Collagen Content in Collagen Sponges and Fleeces

25–30 mg (exactly weighed out) of sample were introduced into 30 ml 0.1M sodium hydrogen carbonate solution (pA, Merck, Darmstadt) pH 8.2 to which 1.5 ml of a 6 mg/ml trypsin solution (lyophilised preparation from bovine pancreas, Boehringer, Mannheim) and incubated for 8 hours at 23±1° C. in a shaking water bath (Julabo SWI, Seelbach). After cooling the sample in a cold room to 4° C., it was centrifuged at 4° C. in a 60 Ti-Rotor (Beckman, Munich) at 32000 RpM for 30 minutes. The residue was filtered in a stirred ultra filtration cell (Mod 8010, Amicon, Witten) through a Diaflow-Filter PM 10 (Amicon, Witten) of diameter 25 mm and 1 ml of the filtrate was hydrolysed in 6HCl for 20 hours at 105° C. The further working up and analysis of the hydrolysate is identical with that described under (1) above with the exception that the further uptake of the sample after twice evaporating to dryness, was in 150 $\mu$l loading buffer, whereby 150 $\mu$l was injected into the test cartouche of the amino acid analyser. The hydroxyproline value obtained after the amino acid analysis (in $\mu$mol/g starting substance), represents the part of the degradable collagen in the sample. When the hydroxyproline value of a parallel hydrolysis (6M HCl) and analysed sample (see (1) above) which represents the total collagen content, is compared with the hydroxyproline value, the percentage proportion of the "native", that is trypsin non-degradable collagen is indicated.

The results are shown in the following table.

TABLE

|  | $\mu$mol/g | mol/1000 mol |
|---|---|---|
| Hydroxyproline | 795.4 | 97 |
| Aspartic acid | 381.7 | 47 |
| Threonine | 190.1 | 23 |
| Serine | 257.0 | 31 |
| Glutamic acid | 691.3 | 84 |
| Proline | 913.2 | 112 |
| Glycine | 2614.6 | 320 |
| Alanine | 864.9 | 106 |
| Cysteine/2 | 11.5 | 2 |
| Valine | 195.7 | 24 |
| Methionine | 62.7 | 8 |
| Isoleucine | 92.8 | 11 |
| Leucine | 229.9 | 28 |
| Tyrosine | 27.0 | 3 |
| Phenylalanine | 119.9 | 15 |
| Histidine | 39.8 | 5 |
| Hydroxylysine | 126.4 | 15 |
| Lysine | 173.5 | 21 |
| Arginine | 395.5 | 48 |
| Total | 8182.9 | 1000 |
| Glucosamine | 9.68 | 1.18 |
| Galactosamine | 46.30 | 5.66 |
| Total Hydroxyproline | 795.4 $\mu$mol/g |  |
| Trypsin-degradable hydroxyproline | 36.9 $\mu$mol/g |  |
| "Native" collagen content | 95.4 % |  |

What is claimed is:
1. A resorbable extracellular matrix for reconstruction of cartilage tissue, said matrix consisting essentially of a purified collagen II derived from natural cartilage tissue from which non-collagen proteins have been removed, wherein said natural cartilage tissue is subjected to defatting, wherein said matrix consists essentially of fibres of native collagen II which are physiologically acceptable for implant into a mammalian body, wherein said matrix carries a material selected from the group consisting of at least one glycosaminoglycan (GAG), chondronectin, anchorin II, cartilage inducing factor (CIF), insulin-like growth factor (IGF), transforming growth factor β (TGFβ) and a mixture thereof.

2. The matrix of claim 1 wherein said GAG is selected from the group consisting of chondroitin sulphate, keratan sulphate, dermatan sulphate, hyaluronic acid, and a mixture thereof.

3. A matrix as claimed in claim 1 which is derived from hyaline cartilage from pig.

* * * * *